United States Patent [19]

Fearnot et al.

[11] Patent Number: 4,945,909
[45] Date of Patent: Aug. 7, 1990

[54] PACEMAKER WITH ACTIVITY-DEPENDENT RATE LIMITING

[75] Inventors: Neal E. Fearnot, West Lafayette, Ind.; Kevin S. Heggs, Monroeville, Pa.; William L. Johnson, Kittanning, Pa.; Donald A. Stevens, Spring Church, Pa.

[73] Assignees: Cook Pacemaker Corporation, Leechburg, Pa.; Medical Engineering & Development Institute, Inc., West Lafayette, Ind.

[21] Appl. No.: 362,064

[22] Filed: Jun. 6, 1989

[51] Int. Cl.[5] ............................................... A61N 1/00
[52] U.S. Cl. ............................................. 128/419 PG
[58] Field of Search ......... 128/419 PG, 419 P, 419 D

[56] References Cited

U.S. PATENT DOCUMENTS

| | | | |
|---|---|---|---|
| 4,140,132 | 2/1979 | Dahl | 128/419 PG |
| 4,436,092 | 3/1984 | Cook et al. | 128/419 PG |
| 4,467,807 | 8/1984 | Bornzin | 128/419 PG |
| 4,467,810 | 8/1984 | Vollman | 128/419 PG |
| 4,726,383 | 2/1988 | Cook et al. | 128/786 |
| 4,759,367 | 7/1988 | Callaghan | 128/419 PG |
| 4,782,836 | 11/1988 | Alt | 128/419 PG |
| 4,827,933 | 5/1989 | Koning et al. | 128/419 PG |
| 4,860,751 | 8/1989 | Callaghan | 128/419 PG |
| 4,865,036 | 9/1989 | Chirife | 128/419 PG |

OTHER PUBLICATIONS

Fearnot, NE, et al., "Principles of Exercise Responsive Pacemakers," *IEEE Engineering in Medicine & Biology*, Jun. 1984, pp. 25–29.

Berstein, et al., "Pacing Mode Codes," *Modern Cardiac Pacing*, Futura Publishing Co., Mount Kisco, N.Y. 1985, Chapter 13, pp. 307–322.

*Primary Examiner*—Francis Jaworski
*Assistant Examiner*—George Manuel
*Attorney, Agent, or Firm*—Richard J. Godlewski

[57] ABSTRACT

A pacemaker is disclosed with a pacing rate that is restricted within a range defined by variable upper and lower rate limits that change as a function of the patient's detected level of activity. An indication such as the nonambient temperature of blood is sensed in the right ventricle of the heart to indicate detected activity level. Other activity indications, such as blood oxygen concentration and body motion, either singly or in combination are also disclosed. A control circuit of the pacemaker varies the upper and lower rate limits according to the patient's detected level of activity. The control circuit also varies the atrial and ventricular refractory periods along with the AV delay period in response to detected activity level changes.

38 Claims, 3 Drawing Sheets

PACEMAKER WITH ACTIVITY-DEPENDENT RATE LIMITING

TECHNICAL FIELD

This invention relates to pacemakers and, particularly, to activity-responsive pacemakers.

BACKGROUND OF THE INVENTION

A healthy heart responds to stress and activity such as exercise by increasing cardiac output through increased heart rate and stroke volume. Optimally, a pacemaker would mimic this natural response in all conditions where increased cardiac output is necessary. Conventional fixed-rate pacemakers can provide some degree of exercise tolerance because the myocardium is sometimes healthy enough to increase cardiac output by increasing stroke volume. However, not all patients have an adequate response with stroke volume increases alone. Increasing the pacing rate during exercise significantly increases cardiac output and, consequently, exercise tolerance.

Atrial-triggered pacemakers, also known as P-wave triggered pacemakers and P-wave synchronous pacemakers, theoretically provide the optimal rate response. They sense atrial electrical depolarizations, commonly observed as "P-waves" on an electrocardiograph (EKG), with an electrode in the atrium and pace the ventricle after an appropriate AV delay period that approximates the AV conduction time. These pacemakers help patients tolerate exercise, because the ventricular pacing rate follows the atrial rate, which increases with exercise. Atrial-triggered ventricular pacing is incorporated into the DDD pacemaker, which paces and senses both chambers. Ventricular pacing is triggered after the AV delay period by a sensed atrial event and inhibited by a sensed ventricular event. Atrial pacing is inhibited by a sensed event in either chamber.

The principle of P-wave sensing and delayed ventricular stimulation is straightforward, but its implementation has led to several problems that have yet to be completely overcome. First, the atrial rate is not always a reliable indicator of the optimal pacing rate. Atrial bradycardia and, more importantly, atrial tachycardia occur in some pacemaker patients, and pacing the ventricle at these abnormal rates must be avoided. Second, atrial flutter and fibrillation also render atrial-triggered stimulation detrimental. A third major problem arises in cases of retrograde AV conduction, which is present in an estimated one-third of patients with complete AV block and two-thirds of patients with lesser degrees of block. Pacemaker-mediated tachycardia (PMT) can occur in such cases because a ventricular pulse is conducted from the ventricular electrode along the retrograde conduction path to the atrial electrode where it is sensed as an atrial contraction. The atrial-triggered pacemaker responds by generating another ventricular pulse after another AV delay period. If not prevented, pacemaker-mediated tachycardia can be lethal.

These problems have prompted several modifications of atrial-triggered pacemakers. Maximum ventricular pacing rates are commonly limited so that, in the presence of atrial flutter, fibrillation, or tachycardia, ventricular pacing will either be maintained at a maximum rate or reduced (sharply or slowly) to a minimum rate. Both options sacrifice exercise responsiveness to maintain the ventricular rate within safe limits. Some doctors have sought a balance by setting the upper rate limit high enough to provide some exercise tolerance and yet low enough to preserve some degree of immunity from retrograde conduction. While this approach may be satisfactory in some cases, it is generally undesirable because any compromise introduces some risk of pacemaker-mediated tachycardia.

Two alternative methods of responding to high atrial rates are 2:1 and Wenckebach heart block. These methods involve controlling the atrial refractory period to inhibit sensing of atrial electrical depolarizations above a set maximum atrial rate. In the 2:1 block method, every other "P-wave" is ignored above a maximum atrial rate. U.S. Pat. No. 4,467,810 to Vollmann shows a pacemaker operable in the DDD mode with 2:1 block. Here, the atrial refractory period is set equal to a time interval or period corresponding to the desired maximum atrial rate. Consequently, when the intrinsic atrial rate exceeds the maximum rate, every second "P-wave" will occur during the atrial refractory period and not be sensed. The maximum atrial rate limits the patient's ability to exercise. A patient with a retrograde VA conduction path can suffer PMT when the maximum atrial rate is set for high exercise tolerance, because the atrial alert period is proportionally longer for high rates. Therefore, the probability is higher that artifacts of ventricular pulses will appear at the atrial electrode during the atrial alert period.

The Wenckebach method consists of progressively delaying the ventricular stimulus, effectively increasing the AV delay period until intermittent block occurs, thus lowering the average ventricular rate. The beat-to-beat ventricular rate is erratic, but the average ventricular rate is higher than during 2:1 block.

Modifications of the atrial-triggered pacemaker have not fully overcome its limitations. Pacemakers are being developed which employ an indicator other than the atrial rate to determine metabolic need. Proposed indicators of activity include nerve action potential frequency, Q-T interval, hydrogen-ion concentration (pH), venous oxygen saturation, respiratory rate, stroke volume, body motion, and body temperature. Proposed pacemakers responsive to these indicators are discussed in an article entitled, "Principles of Exercise Responsive Pacemakers" by Fearnot, Geddes and Smith, on pp. 25-29 of the June, 1984, issue of IEEE Engineering in Medicine and Biology Magazine. Problems with sensitivity, accuracy, and transducer reliability and power consumption impede the practical implementation of some of these techniques. Moreover, optimal pacemaker response is difficult to attain because physiological indicators which vary in response to exercise and stress often exhibit similar variations in response to other conditions not affecting cardiac output requirements. Algorithms have been designed to differentiate between certain true and false indications of exercise, but such algorithms are generally complex because responses to many conditions vary widely from patient to patient. Furthermore, algorithm efficacy is difficult to verify, particularly in human tests, and an algorithm designed to solve one problem may actually introduce others.

The pacemaker shown in U.S. Pat. No. 4,436,092 to Cook et al. controls the heart stimulation rate according to an algorithm relating heart rate to right ventricular blood temperature. It generates stimulation pulses at a demand rate in the absence of natural cardiac activity occurring at a higher rate. The responsiveness of this pacemaker to exercise has been demonstrated, yet its control algorithm does not change pacing rate limits as a function of exercise level.

Bornzin, in U.S. Pat. No. 4,467,807, discloses a rate-adaptive demand pacemaker in which the level of oxygen within intracardiac or pulmonary-artery venous blood determines the escape interval for demand pacing. As such, a given minimum rate is determined for a given oxygen level. FIG. 5 of the Bornzin patent shows an atrial-triggered pacemaker incorporating this rate-determining technique. Although the minimum rate is adjustable, no provision for maximum rate behavior is disclosed.

SUMMARY OF THE INVENTION

The foregoing problems are solved and a technical advance is achieved with a pacemaker that varies the limits of a pacing rate according to the patient's level of activity. Advantageously, the pacemaker includes a control circuit that is responsive to an activity signal indicative of a patient's level of activity for varying an upper rate limit of the pacemaker. A pacing circuit included in the pacemaker is responsive to the upper rate limit for electrically stimulating the heart such as the ventricle thereof at a pacing rate restricted by the upper rate limit. As the patient's level of activity increases, the control circuit advantageously increases the upper rate limit to permit the heart to be stimulated safely at an elevated pacing rate. The increased level of activity correspondingly increases the demand for greater cardiac output which is facilitated by an increase in the pacing rate. An electrical sensing circuit also included in the pacemaker produces a control signal indicative of a predetermined electrical activity of the heart such as an electrical depolarization in the atrium, commonly observed as a "P-wave" on an electrocardiograph (EKG), for controlling the pacing rate of the pacing rate circuit. Normally, the pacemaker electrically stimulates the ventricle on demand at the end of an AV delay period after an atrial depolarization on a one for one basis.

Illustratively, an activity sensor such as a thermistor is implanted into the heart and connected to the pacemaker for sensing the nonambient blood temperature in the right ventricle of the heart. The nonambient blood temperature in the right ventricle of the heart has been found to be a good indication of the patient's level of activity and the patient's cardiac output requirements. Alternatively or in combination, another activity sensor such as a motion sensor is included with the pacemaker for sensing the motion of the patient's body, which is also an indication of the patient's level of activity.

To maintain the pacing rate of the heart within a safe range, the pacing circuit is further responsive to a lower rate limit for stimulating the heart at a pacing rate restricted by both of the upper and lower rate limits. The control circuit includes a lower rate control unit for varying the lower rate limit also according to the patient's level of activity.

To also vary a number of timing intervals or periods of the pacemaker according to the patient's level of activity, the control circuit advantageously includes a number of control units for individually varying the atrial and ventricular refractory periods and the AV delay period. For the atrial refractory period, the electrical sensing circuit such as an atrial sensing circuit illustratively includes an atrial refractory circuit for inhibiting the atrial sensing circuit for an atrial refractory period after the atrial electrical depolarization. As a consequence, the control circuit includes an atrial refractory control unit for varying the atrial refractory period according to the patient's level of activity.

For the ventricular refractory period, the pacemaker illustratively includes a second electrical sensing circuit such as a ventricular sensing circuit for producing a second control signal indicative of another predetermined electrical activity such as a ventricular electrical depolarization. The ventricular sensing circuit includes a ventricular refractory circuit for inhibiting the ventricular sensing circuit for a ventricular refractory period after the ventricular electrical depolarization. The control circuit further includes a ventricular refractory control unit for varying the ventricular refractory period according to the patient's level of activity.

For the AV delay period, the pacing circuit illustratively includes a delay unit for delaying the electrical stimulation of the ventricle for a predetermined AV delay period after, for example, the atrial electrical depolarization. The control circuit also includes a delay control unit for varying the delay period per a predetermined relationship with the atrial refractory period according to the patient's level of activity.

When the atrial electrical depolarizations or "P-waves" occur at a rate in excess of the upper rate limit, the pacemaker utilizes a Wenckebach or a 2:1 block method to stimulate the ventricle. With the Wenckebach method, the atrial refractory control unit varies the atrial refractory period proportionally with an upper rate limit period which is indicative of the upper rate limit.

With the 2:1 block method, the atrial refractory control unit sets the atrial refractory period substantially equal to the upper rate limit period and varies the atrial refractory period and the upper rate limit period according to the patient's level of activity.

Alternatively, the pacemaker is also programmed to vary either one or both of the upper and lower rates so as to maintain a minimum rate difference with the two limits. This advantageously permits intrinsic atrial depolarizations at elevated rates to control stimulation of the ventricle. This is in contrast to just having the pacemaker stimulate both the atrium and ventricle when the intrinsic atrial is abnormally elevated.

The pacemaker also includes an activity sensing circuit responsive to an indication of the patient's level of activity such as ventricular blood temperature, body motion, and the like, either individually or in combination, for producing the activity signal for the control circuit. Each of these indications is sensed with an appropriate sensor and sent to an indication sensing circuit for producing an indication signal indicative of the indication. One or more of these indication sensing circuits are included in the activity circuit along with a combiner circuit for producing the activity signal. Advantageously, such combinations more closely and naturally approximate the patient's level of activity for the purposes of electrically stimulating the patient's heart.

The pacemaker of the present invention controls the range of pacing rates to allow higher rates during activity and yet retains safer pacing limits during rest. The pacemaker comprises a sensor different from "P-wave" sensors for indicating exercise or the need for increased heart rate, a pacing circuit for pacing the heart through a pacemaker lead, and a control circuit for variably controlling the range of pacing rates of the pacing circuit according to the patient's level of activity. The control circuit is responsive to an indicator of activity such that during exercise the control circuit causes an increase in the pacing rate limits.

DETAILED DESCRIPTION

Figure 1:
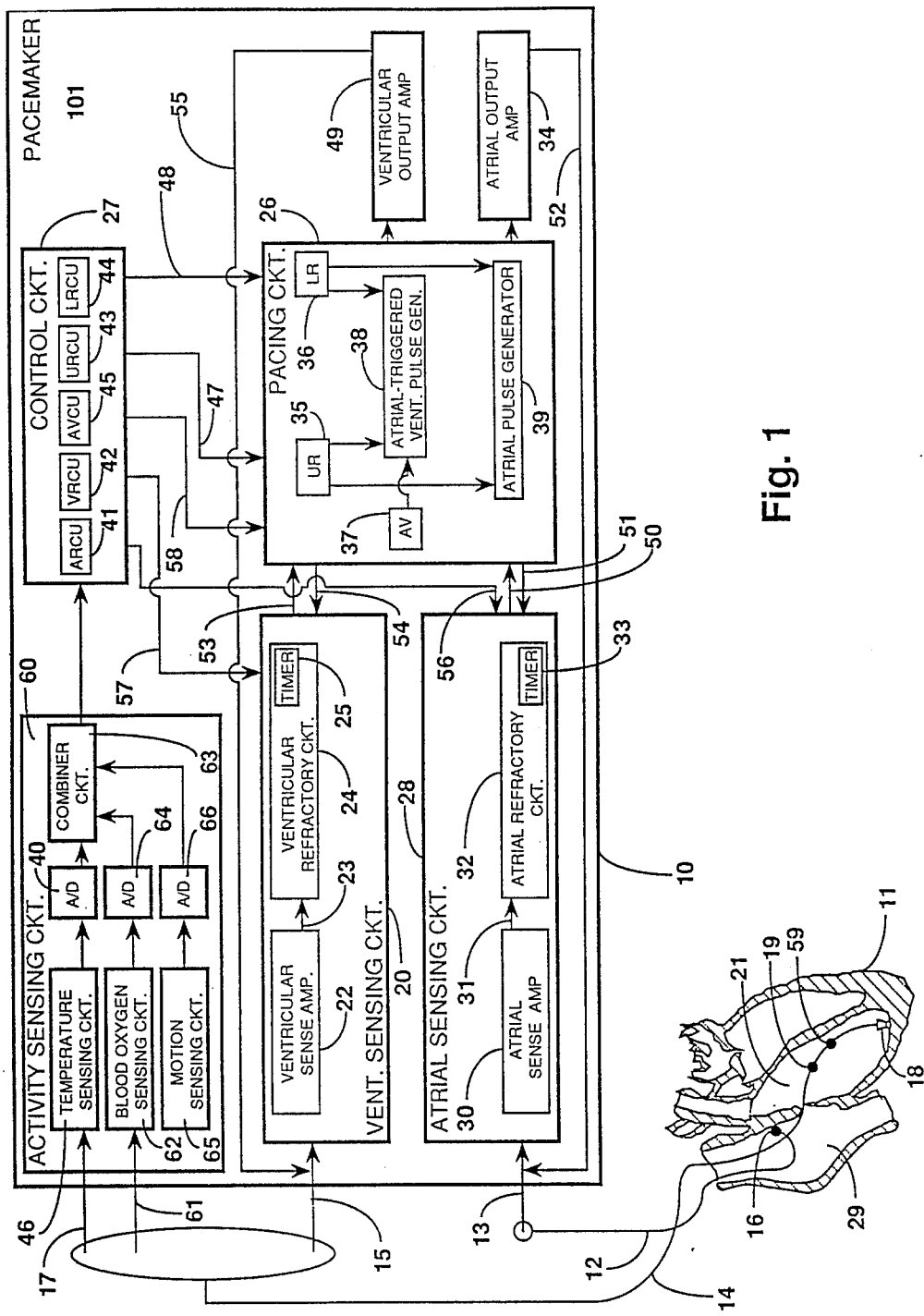
FIG. 1 is a block diagram representation of the preferred embodiment of a cardiac pacemaker of the present invention.

Depicted in FIG. 1 is a cardiac pacemaker 10 for electrically sensing and stimulating a patient's heart 11 at a pacing rate restricted by variable upper and lower rate limits. The pacemaker individually varies the upper and lower rate limits according to the patient's level of activity.

The pacemaker is implanted in a patient and connected to the patient's heart 11 through commercially available atrial catheter 12 and ventricular catheter 14. Activity includes a broad spectrum of activity including, but not limited to, physical, electrical, or chemical activity or a combination of any one or more of these or other individually identifiable activities. Also contemplated is well-known physical exercise involving combinations of muscular, nervous system, vaso, chemical and other physiological and psychological activity.

Pacemaker 10 basically comprises pacing circuit 26, control circuit 27, and atrial sensing circuit 28. Atrial sensing circuit 28 is an electrical activity sensing circuit and is responsive to the electrical activity in right atrium 29 of the heart for producing an atrial output control signal indicative of a predetermined electrical activity such as an atrial electrical depolarization. This atrial depolarization is commonly represented by or observed as a "P-wave" on a electrocardiograph (EKG). The pacemaker senses and paces the right atrium through atrial pacing and sensing lead 13 contained within the atrial catheter and terminated at the distal end in an atrial electrode 16 positioned against a wall of the atrium. At the proximal end, atrial lead 13 connects to atrial sensing circuit 28.

Pacing circuit 28 is responsive to upper and lower rate limits and the atrial output control signal for electrically stimulating the right atrium and right ventricle 21 of the heart on demand at a pacing rate restricted by the upper and lower rate limits. Control circuit 27 varies the upper and lower rate limits according to the patient's level of activity such as physical exercise in response to an indication other than the sensed atrial electrical activity. One such indication or indicator is the nonambient temperature of blood in the right ventricle as described in U.S. Pat. No. 4,726,383. Other indicators related to exercise or a need for increased cardiac output may alternatively be employed such as hydrogen ion concentration (pH), venous oxygen saturation, respiratory rate, right ventricular impedance, stroke volume, minute volume, cardiac output, body acceleration or motion, and nerve impulses.

Pacemaker 10 senses and paces the ventricle through ventricular pacing and sensing lead 15 that is contained within ventricular catheter 14 and terminated at the distal end in ventricular electrode 18 positioned in the apex of the right ventricle. At the proximal end, ventricular lead 15 connects to ventricular sensing circuit 20. Ventricular catheter 14 also contains temperature sensing lead 17 terminated at the distal end by temperature sensor 19 for sensing an indication such as the nonambient temperature of blood in the right ventricle which is indicative of the patient's level of activity or the need for increased cardiac output. At the proximal end, temperature lead 17 connects to an activity indication sensing circuit such as temperature sensing circuit 46 that is included in activity sensing circuit 60. Sensor 19, which is preferably a thermistor, senses the temperature of blood in right ventricle 21. Although temperature sensor 19 is preferably enclosed in ventricular catheter 14, it may alternatively be enclosed in atrial catheter 12 or in a separate catheter. Also included in ventricular catheter 14 is sensing lead 61 terminated at the distal end by blood oxygen sensor 59 and at the proximal end by another activity indication sensing circuit such as blood oxygen sensing circuit 62.

Atrial sensing circuit 28 is a well-known circuit and includes atrial sense amplifier 30 and atrial refractory circuit 32 interconnected by conductor 31. Atrial sense amplifier 30 filters and amplifies the electrical activity sensed by atrial electrode 16 over a predetermined bandwidth. Atrial refractory circuit 32 inhibits or prevents the electrical sensing circuit from indicating atrial electrical activity that occurs during the atrial refractory period after the detection of an atrial electrical depolarization. Atrial refractory circuit 32 includes atrial refractory timer 33 which is responsive to an atrial refractory signal received from control circuit 27 via conductor 56. The atrial refractory signal indicates an atrial refractory period for timer 33. Control circuit 27 includes an atrial refractory control unit (ARCU) 41 for varying the atrial refractory period according to the patient's level of activity or exercise. The atrial refractory circuit produces the atrial output control signal on conductor 50 to the pacing circuit in response to the sensing or detection of an atrial depolarization. The sensing or detection of an atrial depolarization also resets atrial refractory timer 33 in a well-known manner to time the atrial refractory period. Pacing circuit 26 also resets the atrial refractory timer via conductor 51.

Atrial pacing and sensing lead 13 is connected to atrial sense amplifier 30 which is in turn connected to pacing circuit 26 through atrial refractory circuit 32 and conductor 50. In response to atrial pulses generated by the pacing circuit, well-known atrial output amplifier 34 electrically stimulates the atrium via conductor 52 and atrial pacing lead 13.

Pacemaker 10 further includes ventricular sensing circuit 20. Similar to atrial sensing circuit 28, the ventricular sensing circuit is responsive to the electrical activity in right ventricle 21 of the heart for producing a ventricular output control signal which is indicative of predetermined electrical activity such as a ventricular electrical depolarization. The ventricle depolarization is commonly represented by or observed as a "QRS-complex" on an EKG. Ventricular sensing circuit 20 is also a well-known circuit and includes ventricular sense amplifier 22 and ventricular refractory circuit 24 interconnected by conductor 23. Ventricular sense amplifier 22 filters and amplifies the electrical activity sensed by ventricular electrode 12 over a predetermined bandwidth. The ventricular refractory circuit inhibits or prevents the ventricular sensing circuit from indicating to the pacing circuit ventricular electrical activity that occurs during the ventricular refractory period after the detection of a ventricular electrical depolarization.

Ventricular refractory circuit 24 includes ventricular refractory timer 25 which is responsive to a ventricular refractory signal from control circuit 27 via conductor 57. The ventricular refractory signal indicates a variable ventricular refractory period for timer 25. Control circuit 27 further includes a ventricular refractory control unit (VRCU) 42 for varying the ventricular refractory period according to the patient's level of activity. The ventricular refractory circuit produces the ventricular output control signal on conductor 53 to the pacing circuit in response to the sensing or detection of a ventricular electrical depolarization. The sensing or detection of the ventricular depolarization also resets ventricular refractory timer 25 in a well-known manner to time the ventricular refractory period. Pacing circuit 26 also resets the ventricular refractory timer via conductor 54.

Ventricular pacing and sensing lead 15 is connected to ventricular sense amplifier 22 which is in turn connected to pacing circuit 26 through ventricular refractory circuit 24 and conductor 53. In response to ventricular pulses generated by the pacing circuit, well-known ventricular output amplifier 49 electrically stimulates the ventricle via conductor 55 and ventricular lead 15.

Pacing circuit 26 is also a well-known circuit and includes an atrial-triggered ventricular pulse generator 38 for generating ventricular pacing pulses on demand after an AV delay period, in response to a sensed atrial electrical activity. The pacing circuit also includes well-known upper rate circuit 35, lower rate circuit 36, and AV delay circuit 37, which store an upper rate limit, a lower rate limit, and an AV delay period, respectively. Upper rate control unit (URCU) 43, lower rate control unit (LRCU) 44, and AV delay control unit (AVCU) 45 are included in control circuit 27 and vary the upper rate limit, the lower rate limit, and the AV delay period, respectively. Upper rate control unit 43, lower rate control unit 44, and AV delay control 45 control respective upper rate, lower rate, and AV delay circuits 35-37 via conductors 47, 48 and 58, respectively.

The pacing circuit also includes atrial pulse generator 39 for generating atrial pacing pulses on demand. The pacing circuit also includes other well-known units which have not been included to simplify the drawing. Pacing circuit 26 preferably operates in the DDD mode, although DDI, VDD or similar pacing modes which vary the ventricular pacing rate based on the atrial rate are also suitable. The ventricular pacing rate is preferably determined by the atrial pacing rate but restricted by the variable upper and lower rate limits.

Dual-chamber pacing circuits such as pacing circuit 26 are well-known in the art and typically include atrial and ventricular channels for sensing and pacing the atrium and ventricle of the heart. For compact size considerations, these pacing circuits are typically integrated into one programmed-controlled circuit. As a consequence, the atrial and ventricular sensing circuits such as electrical activity sensing circuits 28 and 20 are also typically included in these integrated circuits. The various refractory and delay periods along with the upper and lower rate limits are commonly stored in registers or memory included with the pacing and sensing circuits. Electrical activity sensing circuits 20 and 28 and pacing circuit 28 differ from these integrated pacing circuits in that the refractory and delay periods along with the upper and lower rate limits are variably controlled via control circuit 27.

A brief description of pacing mode codes along with pictorial codes utilized by the industry for pacemakers and adopted by the North American Society of Pacing and Electrophysiology is described by Berstein et al. in "Pacing Mode Codes," *Modern Cardiac Pacino*, Futura Publishing Company, Mount Kisco, N.Y., 1985, Chapter 13, pp. 307-322. As described elsewhere in the reference and known in the industry, dual-chamber pacemakers may be implemented using a microprocessor and a number of memories for storing program instructions and data. The electrical activity sensing circuits 20 and 28, pacing circuit 26, and control circuit 27 along with the various refractory and delay periods, the upper and lower rate limits, and corresponding rate limit periods are implemented in this illustrative embodiment with a microprocessor and associated memories and programmed to perform the herein described functions.

Temperature sensor 19 is connected to control circuit 27 via temperature sensing circuit 46, analog-to-digital converter 40, and combiner circuit 63. The control circuit converts the activity signal indicative of the sensed temperature of blood in ventricle 21 and a blood temperature history to a corresponding set of upper and lower rate limits, atrial and ventricular refractory periods, and an AV delay period for a pacing rate appropriate for the level of activity or exercise indicated by the sensed blood temperature. As the sensed blood temperature indicates a change in the patient's level of exercise, the control circuit varies the range defined by the upper and lower rate limits in which the atrial and ventricular pacing rates of the pacemaker are permitted to operate for a given level of patient exercise. The control circuit also varies the refractory periods and AV delay period according to the patient's level of activity or exercise indicated by the sensed blood temperature.

Activity sensing circuit also includes well-known blood oxygen sensing circuit 62 which connects to control circuit 27 via analog-to-digital converter 64 and combiner circuit 63. The blood oxygen concentration sensed by sensor 59 is also an indication of the patient's level of activity. The blood oxygen indication is utilized alternatively or in combination with the blood temperature indication per a predetermined algorithm of combiner circuit 63 to produce the activity signal for control circuit 27.

Alternatively or in combination, activity sensing circuit 60 includes still another activity indication sensing circuit such as motion sensing circuit 65 connected to combiner circuit 63 via analog-to-digital converter circuit 66. By way of example, physical activity or body motion sensing circuit 65 includes a miniature piezoelectric crystal in the form of a weighted cantilever arm to detect movement of the patient. When the patient moves, the arm vibrates causing the crystal to produce an electrical signal indicative of the patient's level of activity. The crystal and arm are typically mounted in or about the pacemaker case for sensing body motion. Such a sensor is disclosed, for example, in U.S. Pat. No. 4,140,132; however, other well-known types of motion sensors including accelerometers may alternatively be used.

As previously suggested, one or more activity indications may be utilized individually or in combination to produce the activity signal for control circuit 27. The individual or combined activity indications are utilized to approximate the actual activity level of the patient.

One such combination of temperature and body motion is disclosed in U.S. Pat. No. 4,782,836 in which temperature and motion are alternatively utilized to control a stimulation rate based on the level of patient activity. Reference is made to this patent for disclosing just one example of combiner circuit 63. Other combinations of other activity indications such as respiration, QT interval, and the like as previously discussed are contemplated.

Temperature sensing lead 17 connects thermistor 19 to temperature sensing circuit 46 which is a preamplifier circuit that linearizes the thermistor output signal versus temperature over the temperature range encountered by thermistor 19. Since the resistance across thermistor !9 varies in a known manner with temperature, the output voltage from temperature sensing circuit 46 is an analog representation of the instantaneous right ventricular blood temperature. Analog-to-digital converter 40 converts the analog voltage from temperature sensing circuit 46 to a multiple-bit data word indicative of the sensed right ventricular blood temperature and applies the data word to control circuit 27. Activity indication sensing circuits 62 and 65 and analog-to-digital converters 64 and 66 operate in a similar well-known manner.

Control circuit 27 includes atrial refractory control unit 41, ventricular refractory control unit 42, upper rate control unit 43, lower rate control unit 44, AV delay control unit 45, and other well-known circuitry that has not been shown to simplify the drawing. Each of the control units converts the sensed activity indication such as blood temperature included in the activity signal and an indicator history such as blood temperature history to an appropriate rate limit or time period as derived from experimental test data. As the sensed blood temperature increases, the upper and lower rate control units vary the upper and lower rate limits upward to allow the heart rate to increase as would be expected for an increased level of activity or exercise. As previously described, the upper and lower rate limits define a range in which the heart rate should normally occur for a given level of activity or exercise. When the heart fails to beat at or above the lower rate limit for whatever reason, the pacing circuit and output amplifiers will electrically stimulate the atrium and/or the ventricle on demand at a pacing rate indicated by the lower rate limit. As activity or exercise continues to increase, the lower rate control unit will increase the lower rate limit for the pacing circuit to meet the increased need for a higher pacing rate and cardiac output.

When the atrium naturally beats within the expected range established by the upper and lower rate limits for a given level of exercise, the pacing circuit monitors the electrical activity in the atrium and ventricle to determine the need for electrically stimulating the ventricle. As a result, synchrony between the atrium and ventricle is maintained within the upper and lower rate limit range.

When the naturally occurring atrial rate increases beyond the upper rate limit for a given level of exercise, AV synchrony is no longer maintained, and pacing circuit 26 stimulates the ventricle at a pacing rate restricted by the upper rate limit. Upper rate control unit 43 varies the upper rate limit according to the changes in the sensed patient level of activity or exercise. As the sensed level of activity or exercise increases, atrial and ventricular refractory control units 41 and 42 and AV delay control unit 45 decrease the respective atrial and ventricular refractory periods for atrial and ventricular refractory circuits 32 and 20 and also decrease the AV delay period for AV delay circuit 37.

When the naturally occurring atrial rate exceeds the upper rate limit, the pacing circuit is programmed to pace the ventricle utilizing either well-known 2:1 block or Wenckebach behavior. For Wenckebach ventricular pacing, atrial refractory control unit 41 and upper rate control unit 43 vary respectively the atrial refractory period and the upper rate limit time period per a predetermined relationship such as in a proportional manner. An adaptive relationship is also contemplated. When 2:1 block is desired, the atrial refractory control unit sets the atrial refractory period substantially equal to the upper rate limit time period.

To prevent pacing of both the atrium and ventricle when the lower rate limit would exceed a given upper rate limit, upper and lower rate control units 43 and 44 vary the respective upper and lower rate limits such that a minimum rate difference is maintained therebetween. This allows naturally occurring atrial pulses to control ventricular pacing rather than pacing circuit 26 which would pace both the atrium and the ventricle.

Each of control units 41–45 includes a table of rate limits or time periods that are stored in memory. Under control of a microprocessor, the sensed indications such as blood temperature and the like and associated histories thereof such as blood temperature history along with physician established parameters are utilized to access an associated location in memory to obtain a previously determined and stored rate limit or time period. This well-known operation is commonly referred to as a table—lookup operation. As the sensed temperature or indication varies, each of control units 41–45 varies the rate limit or time period based on the rate limit or time period stored for the given sensed temperature or indication. Control circuit 27 has been described as being separate from pacing circuit 26, but both may be implemented using a single microprocessor and associated memories as is well-known in the art.

Pacemaker 10 controls the upper and lower rate limits when cardiac output requirements are low, so as to maintain a low workload on the heart. High atrial rates during rest constitute arrhythmias and therefore should not be tracked to determine ventricular rate. Also, of course, pacemaker-mediated tachycardia should not be possible during rest. During exercise, typical ventricular rates are different from those during rest, and it is advantageous to allow for only those typical rates during exercise. Increasing the lower rate limit provides a higher minimum rate should atrial tracking be lost, and increasing the upper rate limit allows tracking to higher atrial rates which are typical and legitimate during elevated activity such as exercise. Pacemaker 10 allows high ventricular rates only when elevated activity or exercise is detected. By allowing the ventricular rate to generally follow the atrial rate yet varying the rate limits within which tracking is allowed as a function of temperature or other activity indication, pacemaker 10 provides additional exercise responsiveness over other known pacemakers.

Figure 2:
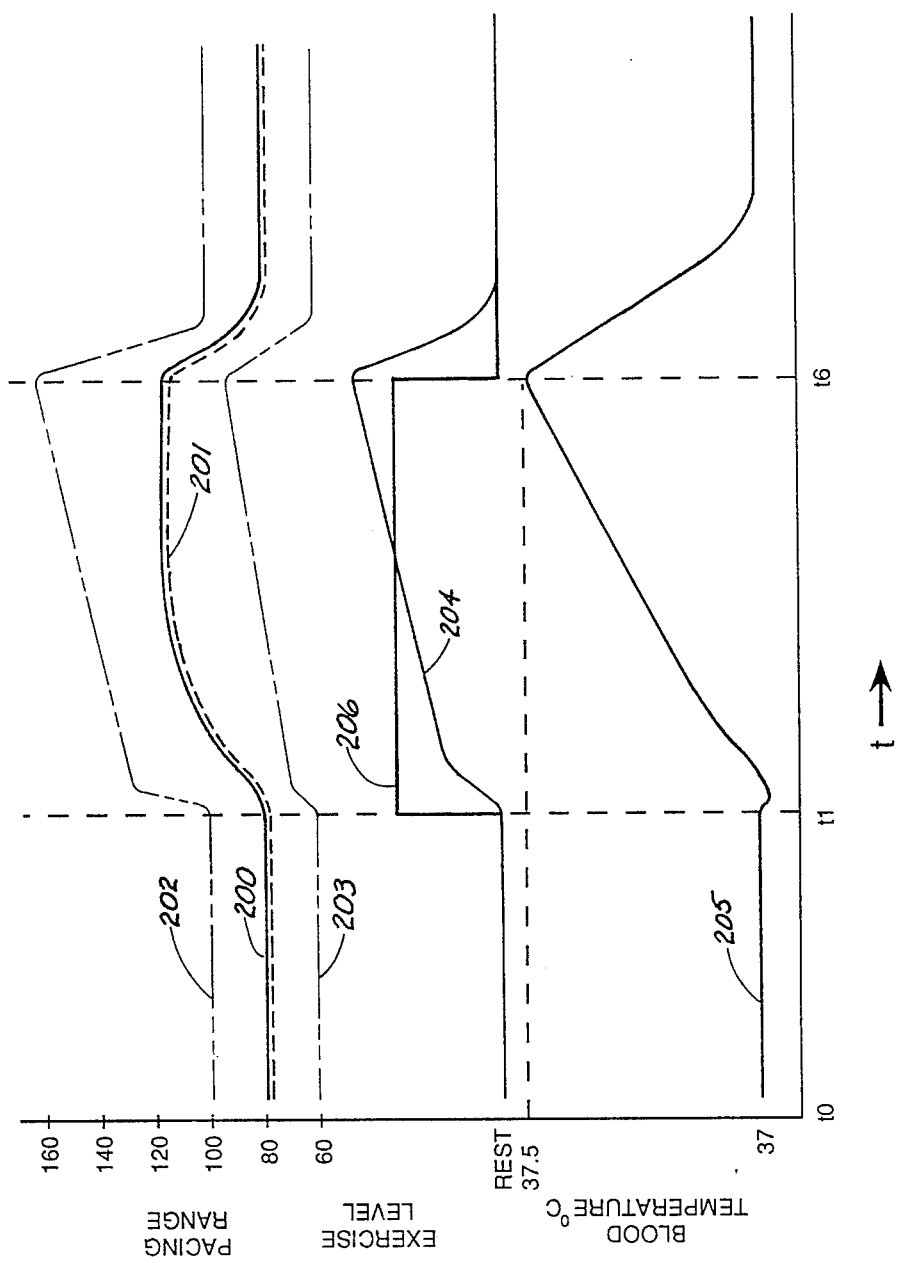
FIG. 2 is a timing diagram demonstrating the concept of changing the range of pacing rate limits during exercise to increase cardiac output of the pacemaker of FIG. 1.

Depicted in FIG. 2 is a graphical example of synchronous atrial intrinsic rate, curve 200, and ventricular pacing rate, curve 201, that occur within a range restricted by an upper rate limit, curve 202, and a lower rate limit, curve 203. The upper and lower rate limits vary according to the patient's detected level of activity or exercise. The detected level of detected activity or exercise and the temperature of blood in the right ventricle of the patient's heart are also illustratively depicted by activity or exercise curve 204 and blood temperature curve 205. The patient's actual level of activity or exercise is depicted by actual exercise curve 206 with an elevated level occurring between times t1 and t6. Assuming the atrial electrical activity is occurring naturally, the ventricular electrical activity is either naturally occurring or being stimulated by pacemaker 10 depending on the sensed ventricular electrical activity and the AV delay interval programmed in the pacemaker. Between times t0 and t1, the patient with AV block is essentially at rest with the atrial intrinsic rate and the ventricular pacing rate occurring at approximately 80 beats per minute with the atrium and ventricle in synchrony. As shown, the upper rate limit, curve 202, is set at 100 beats per minute, whereas the lower rate limit, curve 203, is set at 60 beats per minute. The blood temperature in the right ventricle is approximately 37° C. as shown by blood temperature curve 205.

At time t1, the patient's actual level of exercise, curve 206, assumes a constant level elevated from rest. Thereafter, the blood temperature gradually increases after an initial dip in blood temperature as a result of the increase in the actual activity or exercise level. Since the detected exercise level, curve 204, is a function of the sensed blood temperature, curve 205, the pacemaker responds by correspondingly increasing the upper and lower rate limits, curves 202 and 203. The atrial intrinsic rate, curve 200, and the ventricular pacing rate, curve 201, also increase in response to the increasing blood temperature and detected exercise level.

Between times t1 and t6, the detected exercise level, curve 204, continues to increase essentially tracking the increasing blood temperature. At time t6, the patient stops exercise, curve 206, and the blood temperature and detected exercise level gradually return to a rest level.

As shown, the atrial and ventricular rates, curves 200 and 201, naturally respond to the actual increased level of exercise to meet the demand for increased cardiac output. The pacing range, defined by the upper and lower rate limit curves 202 and 203, smoothly adjust to the blood temperature changes to accommodate the expected atrial intrinsic and ventricular pacing rates.

Figure 3:
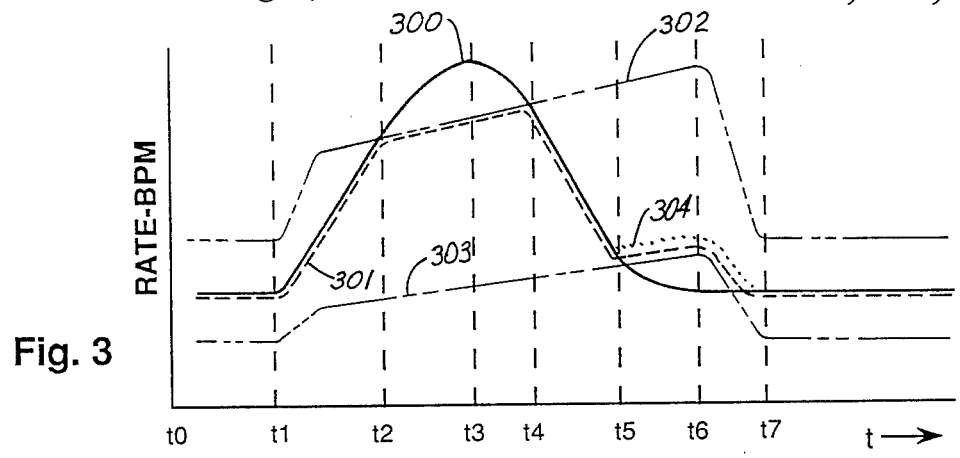
FIGS. 3-5 are timing diagrams illustrating several sets of variable pacing rate limits of the pacemaker of FIG. 1 for various heart conditions.
Figure 4:
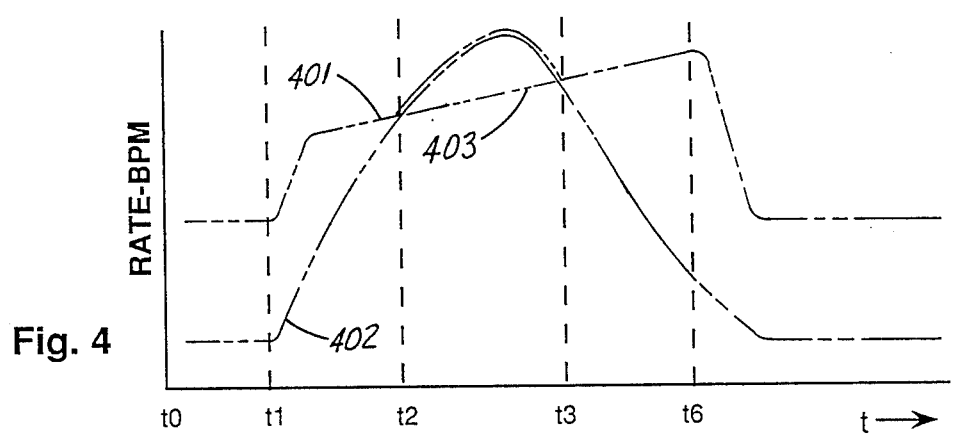
Figure 5:
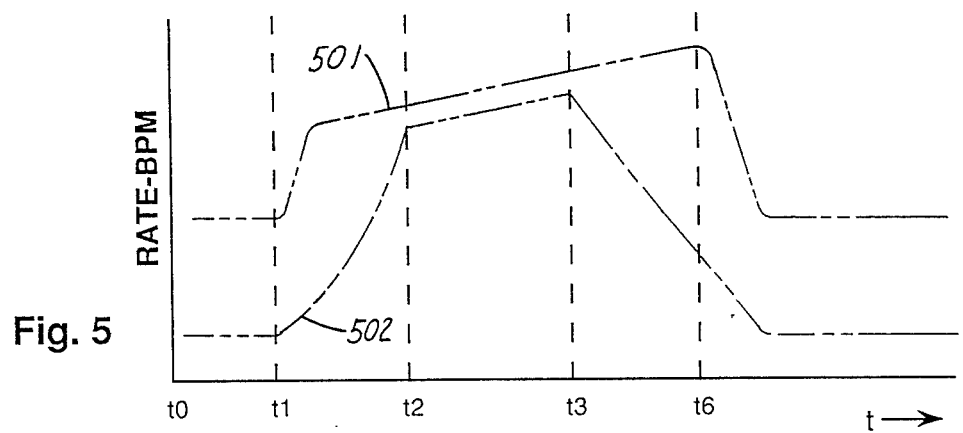

The operation of pacemaker 10 utilizing several different upper and lower rate limit curves for handling several different heart irregularities is illustrated in FIGS. 3-5. The upper and lower rate limit curves 302 and 303 depicted in FIG. 3 are similar to the upper and lower rate curves 202 and 203 depicted in FIG. 2. Between times t1 and t6, the patient assumes a constant elevated level of activity or exercise and experiences a rise in blood temperature as shown by actual exercise level curve 206 and sensed blood temperature curve 205 in FIG. 2, respectively. As a result, the pacemaker detects a level of exercise, as depicted by detected exercise level curve 204 in FIG. 2, as a function of the sensed blood temperature and varies the upper and lower rate limits as depicted by curves 302 and 303 in FIG. 3. However, in the illustration of FIG. 3, the atrial intrinsic rate, curve 300, will experience tachycardia between times t2 through t4 and bradycardia between times t5 through t7.

At time t1, the atrial intrinsic rate, curve 301, increases and reaches a maximum at time t3 in response to the patient's elevated exercise level. Assuming total AV block, pacemaker 10 paces the ventricle in synchrony with the atrium as shown by ventricular pacing rate curve 301 between times t1 and t2. Between times t2 and t4, the atrial intrinsic rate exceeds the upper rate limit, curve 302, for the detected exercise level, and pacemaker 10 restricts the pacing of the ventricle at the upper rate limit. During this time period, the atrium and ventricle are not in synchrony.

At time t4, the atrial intrinsic rate has decreased to the upper rate limit and continues to decrease between times t4 through t5 to the lower rate limit, curve 303, at time t5. Between times t4 and t5, the atrial intrinsic rate is between the upper and lower rate limits of the pacemaker, and the pacemaker again stimulates the ventricle at a ventricular pacing rate, curve 301, in synchrony with the atrial intrinsic rate.

Between times t5 through t7, the atrial intrinsic rate is below the lower rate limit with the atrium experiencing bradycardia. However, due to the detected level of activity or exercise, pacemaker 10 stimulates both the atrium and the ventricle in synchrony at an atrial pacing rate, curve 304, and a ventricular pacing rate, curve 301, equal to the lower rate limit, curve 303, which varies according to the detected exercise level.

At time t7, the atrial intrinsic rate equals the lower rate limit, and the pacemaker thereafter stimulates only the ventricle in synchrony with the atrial intrinsic rate.

The various rate and limit curves have been depicted as individual curves having separations therebetween for purposes of identification and illustration. However, when the atrial and ventricular rates are in synchrony or are being restricted by a rate limit, the rates are substantially equivalent, and the rate curves should appear as coincident lines. When restricted by a rate limit curve, the rate curves should also be coincident with the rate limit curve. Such an example would be between times t5 through t7 for curves 301, 303, and 304.

In FIG. 4, the upper and lower rate limits, curves 401 and 402, again vary as a function of the detected exercise level. However, they vary much more independently such that the lower rate limit would be greater than the upper rate limit if not adjusted according to this invention. For example, with chronotropic incompetence, the lower rate limit, curve 402, is set to increase at a much greater rate than the upper rate limit, curve 401, in response to the detected level of exercise such as curve 204 in FIG. 2. If left unchecked, the lower rate limit would exceed the upper rate limit between times t2 and t3 as indicated by phantom line 403. In such instance, the pacemaker would stimulate both the atrium and the ventricle at the lower rate limit. Such a condition could put the heart into fibrillation depending on the intrinsic atrial rate. However, according to this invention, a minimum rate difference is maintained between the upper and lower rate limits as illustrated by upper and lower rate limit curves between times t2 and t3. As a result, the intrinsic atrial pulses control the pacing of the ventricle when they actually occur between the two rate limits of the pacemaker. Otherwise, the pacemaker would stimulate both the atrium and ventricle regardless of the intrinsic atrial rate. In this example, the lower rate limit dominates the upper rate limit and controls the upper pacing rate of the pacemaker.

Depicted in FIG. 5 is another example of upper and lower rate limits, curves 501 and 502, varying as a function of the detected exercise level. Such a set of upper and lower rate limits might be appropriate where the patient is experiencing angina. In such instance, the upper rate limit would be critical and restrict the upper pacing rate. Similar to the example of FIG. 4, a minimum rate difference is maintained between the upper and lower rate limits as illustrated by curves 501 and 502 between times t2 and t3. However, the upper rate limit, curve 501, dominates the lower rate limit, curve 502, and controls the upper pacing rate of the pacemaker.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A pacemaker with activity-dependent rate limiting, comprising:
   electrical sensing circuit means for producing a first control signal indicative of a predetermined electrical activity of a patient's heart;
   pacing circuit means responsive to an upper rate limit and said first control signal for electrically stimulating said heart at a pacing rate restricted by said upper rate limit; and
   control circuit means responsive to an activity signal, from activity sensing circuit means, indicative of a patient's level of activity other than said predetermined electrical activity for varying said upper rate limit according to the patient's level of activity.

2. The pacemaker of claim 1 wherein said pacing circuit means is further responsive to a lower rate limit for electrically stimulating said heart at said pacing rate restricted by both of said upper and lower rate limits and wherein said control circuit means includes lower rate control means for varying said lower rate limit according to the patient's level of activity.

3. The pacemaker of claim 1 wherein said electrical sensing circuit means includes first refractory circuit means for inhibiting said electrical sensing circuit means for a first refractory period after said predetermined electrical activity and wherein said control circuit means includes first refractory control means for varying said first refractory period according to the patient's level of activity.

4. The pacemaker of claim 1 further comprising second electrical sensing circuit means for producing a second control signal indicative of a second predetermined electrical activity of said heart and wherein said pacing circuit means is further responsive to a lower rate limit and said second control signal for electrically stimulating said heart at said pacing rate restricted by said lower rate limit and said control circuit means includes lower rate control means for varying said lower rate limit according to the patient's level of activity.

5. The pacemaker of claim 4 wherein said second electrical sensing circuit means includes second refractory circuit means for inhibiting said second sensing circuit means for a second refractory period after said second predetermined electrical activity and wherein said control circuit means includes second refractory control means for varying said second refractory period according to the patient's level of activity.

6. The pacemaker of claim 5 wherein said pacing circuit means includes delay means for delaying electrically stimulating said heart for a predetermined delay period after said first-recited predetermined electrical activity and wherein said control circuit means includes delay control means for varying said predetermined delay period per a predetermined relationship with said first refractory period according to the patient's level of activity.

7. The pacemaker of claim 3 wherein said pacing circuit means includes delay means for delaying electrically stimulating said heart for a predetermined delay period after said predetermined electrical activity and wherein said control circuit means includes delay control means for varying said predetermined delay period per a predetermined relationship with said first refractory period according to the patient's level of activity.

8. The pacemaker of claim 1 wherein said electrical sensing circuit means includes first refractory circuit means for inhibiting said electrical sensing circuit means for a first refractory period after said predetermined electrical activity, wherein said upper rate limit is indicative of an upper rate limit period, and wherein said control circuit means includes first refractory control means for varying said first refractory period per a predetermined relationship with said upper rate limit period.

9. The pacemaker of claim 1 wherein said electrical sensing circuit means includes first refractory circuit means for inhibiting said electrical sensing circuit means for a first refractory period after said predetermined electrical activity, wherein said upper rate limit is indicative of an upper rate limit period, and wherein said control circuit means includes first refractory control means for varying said first refractory period with said upper rate limit period, said upper rate limit period and said first refractory period being substantially equal.

10. The pacemaker of claim 1 wherein said pacing circuit means is further responsive to a lower rate limit for electrically stimulating said heart at said pacing rate restricted by both of said upper and lower rate limits and wherein said control circuit means includes lower rate control means for varying said lower rate limit to within a minimum rate difference of said upper rate limit.

11. The pacemaker of claim 1 wherein said pacing circuit means is further responsive to a lower rate limit for electrically stimulating said heart at said pacing rate restricted by both of said upper and lower rate limits and wherein said control circuit means includes lower rate control means for varying said lower rate limit according to the patient's level of activity, one of said upper and lower rate limits being varied to within a minimum rate difference of the other.

12. The pacemaker of claim 1 further comprising activity sensing circuit means responsive to the patient's level of activity for producing said activity signal indicative of the patient's level of activity and wherein said control circuit means is responsive to said activity signal for varying said upper rate limit according to the patient's level of activity.

13. The pacemaker of claim 12 wherein said activity sensing circuit means includes temperatures sensing circuit means responsive to a blood temperature in said heart indicative of the patient's level of activity for producing said activity signal.

14. The pacemaker of claim 12 wherein said activity sensing circuit means includes motion sensing circuit means responsive to a motion of a patient's body indicative of the patient's level of activity for producing said activity signal.

15. The pacemaker of claim 12 wherein said activity sensing circuit means includes a first indication sensing circuit means responsive to a first indication indicative of the patient's level of activity for producing a first indication signal indicative of said first indication.

16. The pacemaker of claim 15 wherein said activity sensing circuit means includes a second indication sensing circuit means responsive to a second indication indicative of the patient's level of activity for producing a second indication signal indicative of said second indication.

17. The pacemaker of claim 16 wherein said activity sensing circuit means further includes combiner circuit means responsive to said first and second indication signals and a predetermined combinational algorithm for producing said activity signal.

18. A pacemaker with activity-dependent rate limiting, comprising:
an atrial sensing circuit responsive to electrical activity in an atrium of a patient's heart for producing a first control signal indicative of a predetermined atrial electrical activity;
a pacing circuit responsive to said first control signal and an upper rate limit for electrically stimulating a ventricle of said heart subsequent to said predetermined atrial electrical activity and at a ventricular pacing rate limited by said upper rate limit; and
a control circuit responsive to an activity signal, from activity sensing circuit means, indicative of the patient's level of activity and including an upper rate limit control unit for varying said upper rate limit according to the patient's level of activity.

19. The pacemaker of claim 18 wherein said pacing circuit is further responsive to a lower rate limit for electrically stimulating said ventricle at said ventricular pacing rate limited by both of said upper and lower rate limits and wherein said control circuit further includes a lower rate limit control unit for varying said lower rate limit according to the patient's level of activity.

20. The pacemaker of claim 19 wherein said pacing circuit includes a delay circuit for delaying electrically stimulating said ventricle for a predetermined delay period after said predetermined atrial electrical activity and wherein said control circuit further includes a delay control unit for varying said predetermined delay period according to the patient's level of activity.

21. The pacemaker of claim 20 further comprising an atrial refractory circuit for inhibiting said atrial sensing circuit for an atrial refractory period after said redetermined atrial electrical activity.

22. The pacemaker of claim 21 wherein said control circuit further includes an atrial refractory control unit for varying said atrial refractory period according to the patient's level of activity.

23. The pacemaker of claim 22 further comprising a ventricular sensing circuit responsive to electrical activity in said ventricle for producing a second control signal indicative of a predetermined ventricular electrical activity and wherein said pacing circuit is further responsive to said second control signal for electrically stimulating said ventricle on demand after said predetermined delay period.

24. The pacemaker of claim 22 further comprising a ventricular refractory circuit for inhibiting said ventricular sensing circuit for a ventricular refractory period after said predetermined ventricular electrical activity.

25. The pacemaker of claim 24 wherein said control circuit further includes a ventricular refractory control unit for varying said ventricular refractory period according to the patient's level of activity.

26. The pacemaker of claim 25 further comprising a temperature sensing circuit responsive to a blood temperature in said ventricle for producing said activity signal indicative of the patient's level of activity and wherein said control circuit is responsive to said activity signal for varying said upper rate limit.

27. The pacemaker of claim 25 further comprising a motion sensing circuit responsive to a motion of the patient's body indicative of the patient's level of activity for producing said activity signal indicative of the patient's level of activity and wherein said control circuit is responsive to said activity signal for varying said upper rate limit.

28. The pacemaker of claim 25 further comprising:
a temperature sensing circuit responsive to a blood temperature in said ventricle for producing a first indication signal indicative of the patient't level of activity;
a motion sensing circuit responsive to a motion of patient's body for producing a second indication signal indicative of the patient's level of activity;
a combiner circuit responsive to said first and second indication signals and a predetermined combinational algorithm for producing said activity signal; and
wherein said control circuit is responsive to said activity signal for varying said upper rate limit.

29. An atrioventricular pacemaker with activity-dependent rate limiting, comprising:
an atrial sensing circuit response to electrical activity in a patient's heart for producing a first control signal indicative of an atrial depolarization;
an atrial refractory circuit for inhibiting said atrial sensing circuit for an atrial refractory period after said atrial depolarization;
an atrial refractory control unit responsive to a blood temperature in said heart indicative of the patient's level of activity for varying said atrial refractory period according to the patient's level of activity;
an upper rate limit control unit responsive to said blood temperature for varying an upper rate limit according to the patient's level of activity;
a lower rate limit control unit responsive to said blood temperature for varying a lower rate limit according to the patient's level of activity;
a ventricular sensing circuit responsive to said electrical activity for producing a second control signal indicative of a ventricular depolarization;
a ventricular refractory circuit for inhibiting said second sensing circuit for a ventricular refractory period;
a ventricular refractory control unit responsive to said blood temperature for varying said ventricular refractory period according to the patient's level of activity;
a pacing circuit responsive to said first and second control signals for electrically stimulating an atrium and a ventricle of said heart on demand at a pacing rate limited by said upper and lower rate limits;
a delay circuit responsive to said first control signal for delaying electrically stimulating said ventricle for a predetermined delay period after said atrial depolarization; and a delay control unit responsive to said blood temperature for varying said delay period according to the patient's level of activity.

30. An atrioventricular pacemaker with activity-dependent rate limiting, comprising:

first sensing means for sensing electrical activity in a patient's heart, said sensing means including means for detecting predetermined electrical activity indicative of a P-wave;

second sensing means for sensing a patient's level of activity other than said predetermined electrical activity;

control circuit means coupled to said second sensing means for generating an upper and a lower rate limit for the patient's level of activity; and pacing circuit means for generating a ventricular pulse after a predetermined AV delay period in response to detection of said predetermined electrical activity by said first sensing means, whereby the ventricular pulse rate normally equals the sensed atrial rate, said pacing circuit means including means for limiting the ventricular pulse rate to within a range restricted by said upper and lower rate limits, said control circuit means including means for varying said upper rate limit according to the patient's level of activity, whereby the ventricular pulse rate follows the sensed atrial rate up to said upper rate limit determined by the patient's cardiac output requirement.

31. The pacemaker of claim 30 wherein said control circuit means varies both of said upper and lower rate limits in response to the patient's level of activity, whereby the patient's level of activity determines both of said rate limits.

32. The pacemaker of claim 1 wherein said first sensing means includes means for sensing ventricular electrical activity.

33. The pacemaker of claim 32 further comprising atrial refractory circuit means for inhibiting said first sensing means for an atrial refractory period after detection of said predetermined electrical activity by said first sensing means, and wherein said control circuit means increases said upper rate limit and decreases the atrial refractory period when the patient's level of activity increases.

34. The pacemaker of claim 33 wherein said pacing circuit means further includes means for generating atrial pulses in the absence of said predetermined, electrical activity.

35. The pacemaker of claim 30 further comprising atrial refractory circuit means for inhibiting said first sensing means for an atrial refractory period after detection of said predetermined electrical activity by said first sensing means, and wherein said control circuit means increases said upper rate limit and decreases the atrial refractory period when the patient's level of activity increases.

36. The pacemaker of claim 35 wherein said control circuit includes means for varying both of said upper and lower rate limits in response to changes in the patient's level of activity.

37. The pacemaker of claim 36 further comprising third sensing means for sensing ventricular electrical activity.

38. The pacemaker of claim 37 wherein said pacing circuit means further includes means for generating atrial pulses in the absence of said predetermined electrical activity.

* * * * *